(12) United States Patent
Kemp et al.

(10) Patent No.: US 9,421,337 B2
(45) Date of Patent: *Aug. 23, 2016

(54) AUTO-INJECTOR

(75) Inventors: Thomas Mark Kemp, Ashwell (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 516 days.

This patent is subject to a terminal disclaimer.

(21) Appl. No.: 13/877,493

(22) PCT Filed: Oct. 6, 2011

(86) PCT No.: PCT/EP2011/067496
§ 371 (c)(1),
(2), (4) Date: Apr. 3, 2013

(87) PCT Pub. No.: WO2012/045833
PCT Pub. Date: Apr. 12, 2012

(65) Prior Publication Data
US 2013/0190722 A1    Jul. 25, 2013

Related U.S. Application Data

(60) Provisional application No. 61/432,693, filed on Jan. 14, 2011.

(30) Foreign Application Priority Data

Oct. 8, 2010  (EP) .................................... 10186999
Jan. 18, 2011  (EP) .................................... 11151210

(51) Int. Cl.
*A61M 5/32*    (2006.01)
*A61M 5/20*    (2006.01)

(52) U.S. Cl.
CPC ......... *A61M 5/3257* (2013.01); *A61M 5/2033* (2013.01); *A61M 5/3202* (2013.01); *A61M 5/326* (2013.01); *A61M 2005/206* (2013.01); *A61M 2005/2013* (2013.01)

(58) Field of Classification Search
CPC ........... A61M 5/2033; A61M 5/3257; A61M 5/3202; A61M 2005/2013; A61M 2005/206; A61M 5/326; A61M 5/3232
See application file for complete search history.

(56) References Cited

U.S. PATENT DOCUMENTS

| | | | |
|---|---|---|---|
| 2002/0095120 | A1 | 7/2002 | Larsen et al. |
| 2006/0224124 | A1 | 10/2006 | Scherer |
| 2007/0027430 | A1 | 2/2007 | Hommann |
| 2013/0190721 | A1 | 7/2013 | Kemp et al. |

FOREIGN PATENT DOCUMENTS

| | | |
|---|---|---|
| EP | 1743666 | 1/2007 |
| WO | 2009/062508 | 5/2009 |

OTHER PUBLICATIONS

International Search Report for Int. App. No. PCT/EP2011/067496, completedJan. 31, 2012.
International Search Report issued in PCT/EP2011/067493 completed Feb. 8, 2012 (5 pages).
Office Action issued in U.S. Appl. No. 13/877,492 on Jul. 28, 2015 (10 pages).

*Primary Examiner* — Theodore Stigell
(74) *Attorney, Agent, or Firm* — Fish & Richardson P.C.

(57) ABSTRACT

The invention refers to an auto-injector for administering a medicament (M) and to a method for operating it, the auto-injector comprising of a tubular chassis and a carrier subassembly, comprising a tubular carrier slidably arranged in the chassis. The carrier contains a syringe, a drive spring and a plunger for forwarding load of the drive spring to a stopper arranged in the syringe. The syringe is locked for joint axial translation with the carrier. A control spring is connectable to the carrier by first interlock means for needle insertion, wherein the whole carrier subassembly is advanced. Second interlock means are arranged for releasing the drive spring when the carrier has at least almost reached an injection depth thus delivering the medicament (M). The first interlock means are arranged for decoupling the control spring from the carrier and coupling it to the chassis for advancing it over the needle into a needle safe position.

15 Claims, 10 Drawing Sheets

AUTO-INJECTOR

CROSS REFERENCE TO RELATED APPLICATIONS

The present application is a U.S. National Phase Application pursuant to 35 U.S.C. §371 of International Application No. PCT/EP2011/067496 filed Oct. 6, 2011, which claims priority to European Patent Application No. 10186999.8 filed Oct. 8, 2010, Provisional Patent Application No. 61/432,693 filed Jan. 14, 2011, and European Patent Application No. 11151210.9 filed Jan. 18, 2011. The entire disclosure contents of these applications are herewith incorporated by reference into the present application.

TECHNICAL FIELD

The invention relates to an auto-injector for administering a dose of a liquid medicament according to the preamble of claim 1 and to a method for operating an auto-injector.

BACKGROUND OF THE INVENTION

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

High viscosity medicaments require high forces for expelling them through the relatively thin injection needle. To achieve these forces strong drive springs are needed. This can lead to a high impact felt by the user when inserting the needle into the skin and to high forces felt by the user when triggering the injection.

SUMMARY

It is an object of the present invention to provide an improved auto-injector and an improved method for operating an auto-injector.

The object is achieved by an auto-injector according to claim 1 and by a method according to claim 13.

Preferred embodiments of the invention are given in the dependent claims.

In the context of this specification the term proximal refers to the direction pointing towards the patient during an injection while the term distal refers to the opposite direction pointing away from the patient.

According to the invention an auto-injector for administering a dose of a liquid medicament comprises:

a tubular chassis arranged to contain a syringe with a hollow needle and a stopper for sealing the syringe and displacing the medicament, the chassis having a distal end and a proximal end with an orifice intended to be applied against an injection site, wherein the syringe is slidably arranged with respect to the chassis, a drive spring capable of operating the syringe to supply the dose of medicament, a control spring capable of
pushing the needle from a covered position inside the chassis into an advanced position through the orifice and past the proximal end for needle insertion, and
advance the chassis over the needle after at least partially delivering the medicament,
activating means arranged to lock the drive spring and the control spring in a pressurized state prior to manual operation and capable of, upon manual operation, releasing the control spring and/or the drive spring for injection.

A carrier subassembly comprising a tubular carrier, the syringe, the drive spring and a plunger for forwarding load of the drive spring to the stopper is slidably arranged in the chassis. The carrier contains the syringe, the drive spring and the plunger. The syringe is locked for joint axial translation with the carrier. The control spring is connectable to the carrier by first interlock means for needle insertion. Furthermore the first interlock means are arranged for decoupling the control spring from the carrier and coupling it to the chassis for advancing it over the needle into a needle safe position. The activating means comprise second interlock means arranged for releasing the drive spring when the carrier has at least almost reached an injection depth during needle insertion.

The carrier subassembly with the integrated drive spring allows for employing a strong drive spring without any impact on the user when triggering the auto-injector or during needle insertion since these actions are achieved or opposed by the control spring which can be specified considerably weaker than the drive spring. This allows for delivering highly viscous medicaments.

Releasing the drive spring upon the needle reaching an injection depth avoids a so called wet injection, i.e. medicament leaking out of the needle which is a problem in conventional art auto-injectors, where both needle insertion and injection are achieved by pushing on the stopper.

The auto-injector according to the invention has a particularly low part count compared to most conventional auto-injectors thus reducing manufacturing costs. The arrangement with separate control spring and drive spring for fluid injection allows for using one design for different viscosity liquids by just changing the drive spring, and for different volumes just by changing the length of the plunger. This is an advantage over conventional art designs where the drive spring also serves for needle insertion and/or for advancing a shroud.

The activating means may comprise a wrap-over trigger sleeve arranged over the distal end of the auto-injector, the trigger sleeve extending at least almost over the whole length of the auto-injector. The trigger sleeve may be arranged to release the control spring for needle insertion upon translation in proximal direction relative to the chassis.

In order to trigger an injection the auto-injector has to be pressed against an injection site, e.g. a patient's skin. A user, e.g. the patient or a caregiver, grabs the wrap-over trigger sleeve with their whole hand and pushes the chassis protruding from the proximal end against the injection site. Consequently, the trigger sleeve translates in proximal direction relative to the chassis and releases the control spring for starting the injection cycle. The auto-injector according to the invention is particularly well suited for people with dexterity problems since, as opposed to conventional art auto-injectors, triggering does not require operation of small buttons by single fingers. Instead, the whole hand is used.

The first interlock means may be arranged to couple the control spring to either the carrier or the chassis depending on the relative axial position of the carrier and the trigger sleeve, e. g. in a manner to keep the control spring coupled to the carrier during translation of the chassis into the trigger sleeve when the auto-injector is pushed against the injection site, during needle insertion and during injection. When the auto-injector is removed from the injection site at the end of dose or mid injection the trigger sleeve is translated in distal direction relative to the carrier subassembly under load of the control spring. Thus the carrier is in an even more advanced position relative to the trigger sleeve than during injection. In this position the first interlock means decouple the control spring from the carrier and couple it to the chassis for advancing it over the needle into the needle safe position.

Third interlock means may be arranged for coupling the chassis to the carrier for joint axial translation relative to the trigger sleeve depending on a relative axial position of the trigger sleeve and the chassis. The third interlock means may be arranged to decouple the chassis from the carrier upon translation of the trigger sleeve in proximal direction when being pushed against the injection site thus releasing the control spring for needle insertion. Hence, the trigger sleeve has to be translated by a defined distance before the control spring is being released to start an injection cycle.

The control spring may be arranged around the carrier. The first interlock means may comprise a proximal collar arranged around the carrier proximally from the control spring, wherein the control spring acts between the trigger sleeve and the proximal collar. The proximal collar may exhibit at least one pin engageable in a respective first recess in the carrier for coupling the proximal collar to the carrier. The trigger sleeve exhibits a third boss for outwardly supporting the proximal collar so as to prevent decoupling of the pin from the first recess. When the carrier is being removed from the injection site at the end of injection or mid injection, the carrier extends out of the proximal end of the trigger sleeve under load of the control spring, thereby removing the third boss from behind the proximal collar thus causing the pin to decouple from the first recess due to their ramped engagement and to be coupled to the chassis for advancing it over the needle. A ramped engagement in the terminology of this specification is an engagement between two components with at least one of them having a ramp for engaging the other component in such a manner that one of the components is flexed aside when the components are axially pushed against each other provided this component is not prevented from flexing aside.

Fourth interlock means may be arranged for restricting extension of the chassis from the proximal end of the trigger sleeve to an initial pre-injection position. The fourth interlock means may be arranged to disengage upon translation of the carrier subassembly during needle insertion. Prior to injection the chassis is restricted to a first extension from the trigger sleeve, e.g. 6 mm. When the auto-injector has been triggered and the carrier subassembly has been translated for needle insertion the fourth interlock means disengages thus allowing the chassis to be extended beyond that pre-injection position from the chassis for covering the needle, e.g. 16 mm.

The second interlock means may comprise a thrust collar distally arranged on the plunger, wherein the drive spring acts between the thrust collar and the carrier, e.g. a distal carrier end face. At least one first resilient clip may be arranged in the carrier, the first resilient clip proximally engageable behind the thrust collar for preventing translation of the plunger. A first boss in the trigger sleeve is arranged for outwardly supporting the first resilient clip and preventing it from flexing outwards. The first boss is arranged to be removed from behind the first resilient clip on translation of the carrier subassembly at least almost into a maximum proximal position during needle insertion, thereby allowing the first resilient clip to be flexed outwards by the thrust collar due to their ramped engagement under load of the drive spring thus releasing the plunger for injection.

The thrust collar may have a wider diameter than the plunger. Alternatively a circumferential notch may be arranged proximally behind the thrust collar in the plunger for allowing the first resilient clip to engage it.

The third interlock means may comprise at least one second resilient clip on the chassis arranged to be engaged in a respective aperture in the carrier. A respective second boss is arranged in the trigger sleeve for outwardly supporting the second resilient clip and preventing it from flexing outwards. The second boss is arranged to be removed from behind the second resilient clip on translation of the chassis and the carrier subassembly in distal direction relative to the trigger sleeve during manual operation into a position just before the carrier abuts against the trigger sleeve thereby allowing the second resilient clip to flex outwards due to ramped engagement with the carrier under load of the control spring thus releasing the carrier subassembly from the chassis.

The fourth interlock means may comprise at least one third resilient clip on the chassis arranged to abut against a shoulder in the trigger sleeve in proximal direction. A fourth boss is arranged on the carrier for inwardly supporting the third resilient clip and preventing it from flexing inwards. The fourth boss is arranged to be removed from behind the third resilient clip on translation of the carrier subassembly in proximal direction relative to the chassis during needle insertion thereby allowing the third resilient clip to flex inwards due to ramped engagement with the fourth boss under load of the control spring thus allowing the chassis to travel beyond the initial pre-injection position into a needle safe position.

The injection depth may be controlled by the carrier abutting against the chassis during needle insertion and injection resulting in a maximum proximal position of the carrier. The injection depth is therefore unaffected whether or not the chassis is maintained fully depressed during needle insertion.

However, the position of the carrier subassembly would be undefined when the chassis is advanced for needle safety. In order to substantially maintain the maximum proximal position a flange may be arranged on the carrier for abutting against the distal end of the control spring so as to prevent the carrier subassembly from advancing substantially beyond its maximum proximal position when the chassis has been advanced over the needle. The control spring thus acts against both, the chassis in proximal direction and the carrier in distal direction, effectively preventing re-exposure of the needle after the chassis has been advanced into the needle safe position.

In order to ensure needle safety under inertial forces, e.g. when the auto-injector is heavily shaken after use a snap feature may be provided between the chassis and the carrier for locking them together when the chassis is in the needle safe position.

According to another aspect of the invention a method for operating the above described auto-injector comprises the steps of:
- coupling the control spring to the carrier by the first interlock means and preventing release of the drive spring by the second interlock means in the initial state,
- translating the trigger sleeve in proximal direction relative to the chassis when the proximal end of the auto-injector is being pushed against the injection site,
- advancing the carrier subassembly for needle insertion into an injection site upon full translation of the trigger sleeve,
- releasing the drive spring by the second interlock means upon the needle at least almost reaching an injection depth during needle insertion, thereby allowing the drive spring to advance the plunger and the stopper for at least partially delivering the medicament,
- translating the trigger sleeve in distal direction under load of the control spring relative to the carrier subassembly on removal of the auto-injector from the injection site, thereby connecting the control spring to the chassis by the first interlock means,
- advancing the chassis in proximal direction relative to the carrier subassembly into a needle safe position under load of the control spring.

The third interlock means may be released thereby decoupling the chassis from the carrier upon translation of the trigger sleeve in proximal direction thus releasing the control spring for needle insertion.

The fourth interlock means may be disengaged upon translation of the carrier subassembly during needle insertion.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
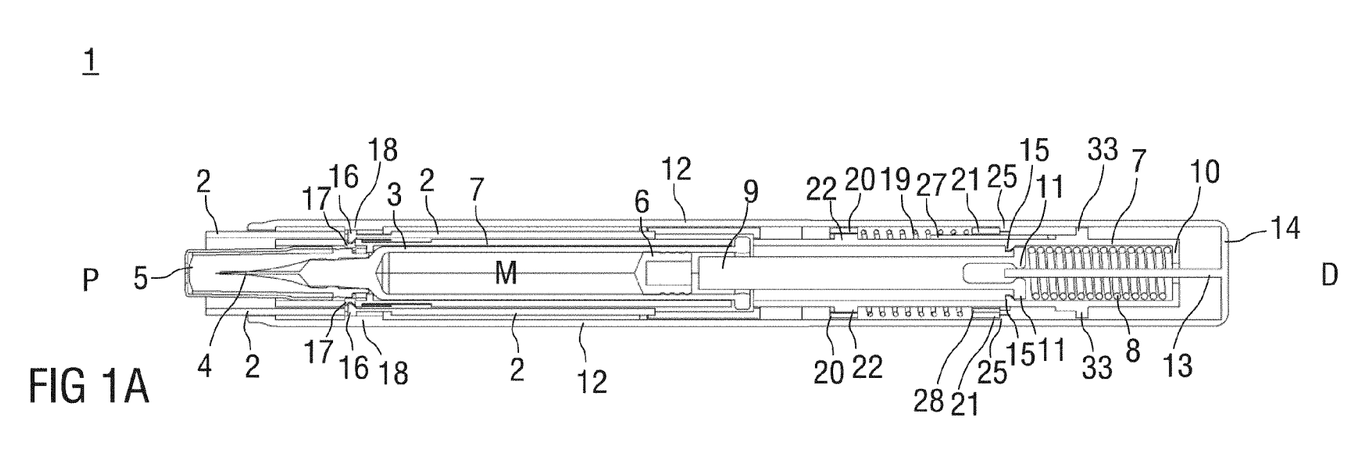
FIG. 1 is an auto-injector with a syringe in an initial state prior to actuation.
Figure 1B:
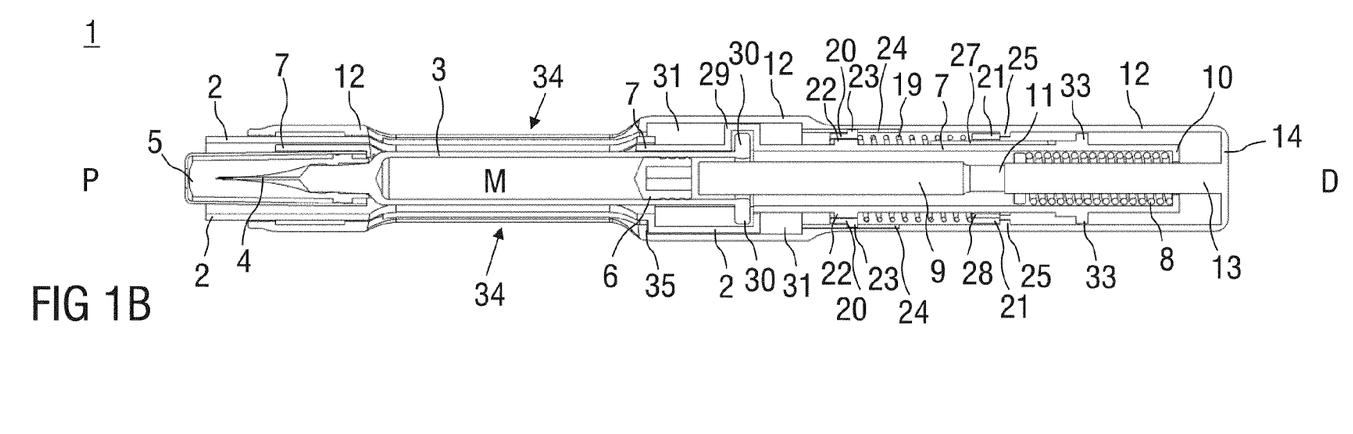

FIG. 1 shows two longitudinal sections in different section planes of an auto-injector 1, the different section planes approximately 90° rotated to each other, wherein the auto-injector 1 is in an initial state prior to starting an injection. The auto-injector 1 comprises a chassis 2. A syringe 3, e.g. a Hypak syringe, with a hollow injection needle 4 is arranged in a proximal part of the auto-injector 1. When the auto-injector 1 or the syringe 3 is assembled a protective needle shield 5 is attached to the needle 4. A stopper 6 is arranged for sealing the syringe 3 distally and for displacing a liquid medicament M through the hollow needle 4. The syringe 3 is held in a tubular carrier 7 and supported at its proximal end therein. The carrier 7 is slidably arranged in the chassis 2.

A drive spring 8 in the shape of a compression spring is arranged in a distal part of the carrier 7. A plunger 9 serves for forwarding the force of the drive spring 8 to the stopper 6.

The drive spring 8 is loaded between a distal carrier end face 10 of the carrier 7 and a thrust collar 11 arranged distally on the plunger 9.

A wrap-over trigger sleeve 12 is arranged over the distal end D of the auto-injector 1 extending almost over the whole length of the auto-injector 1. Outwardly the thrust collar 11 is held behind two first resilient clips 15 in the carrier 7 in a manner to prevent translation of the plunger 9 in proximal direction P. The first resilient clips 15 are distally ramped in a manner to let the thrust collar 11 flex them outwards under load of the drive spring 8. However, in the initial state the first resilient clips 15 are prevented from flexing outwards by respective first bosses 13 in the trigger sleeve 12.

The carrier 7 is locked to the chassis 2 near the proximal end P of the auto-injector 1 by two second resilient clips 16 on the chassis 2 engaged in respective apertures 17 in the carrier 7. In the initial state the second resilient clips 16 are outwardly supported by respective second bosses 18 in the trigger sleeve 12 so as to prevent the second resilient clips 16 from flexing outwards and disengaging the carrier 7 from the chassis 2.

A control spring 19 in the shape of another compression spring is arranged around the carrier 7 and acts between a proximal collar 20 and a rib 21 on the inner surface of the trigger sleeve 12. The proximal collar 20 is engaged with a pin 22 in a first recess 23 in the carrier 7 thus coupling the proximal collar 20 to the carrier 7 for joint axial translation. A third boss 24 in the trigger sleeve 12 is arranged to support the proximal collar 20 outwardly in a manner to prevent disengagement of the pin 22 from the first recess 23. Therefore the load from the proximal end of the control spring 19 is coupled through to the carrier 7 in the initial state.

The trigger sleeve 12 is enabled to move in proximal direction P with respect to the carrier 7 against the force of the control spring 19. As the carrier 7 is initially locked to the chassis 2, translation of the trigger sleeve 12 in proximal direction P relative to chassis 2 compresses the control spring 19. The extension of the trigger sleeve 12 in distal direction D relative to the chassis 2 is defined by two third resilient clips 25 on the chassis 2 abutting against a first shoulder 26 on the trigger sleeve 12 in proximal direction P. In the initial state the third resilient clips 25 are inwardly supported by a fourth boss 27 on the carrier 7 in a manner to prevent them from flexing inwards and advance beyond the first shoulder 26.

A sequence of operation of the auto-injector 1 is as follows:

The protective needle shield 5 is removed from the proximal end P. The needle 4 is now exposed but still a safe distance back within the chassis 2 to protect the user from accidental needle stick injuries. The carrier 7 exhibits a retainer pocket 29 for accommodating a finger flange 30 of the syringe 3. The trigger sleeve 12 comprises a widened portion 31 for accommodating the retainer pocket 29 in a manner to restrict relative rotation of the trigger sleeve 12 and the carrier 7 while allowing translation in longitudinal direction. Thus rotation of the needle 4 is prevented.

Any axial load applied to the carrier 7 during removal of the protective needle shield 5 is resolved through the carrier 7 locked to the chassis 2 by the second resilient clip 16. As the protective needle shield 5 is being removed axial load applied to the chassis 2 is resolved via third resilient clips 25 and first shoulder 26 through the trigger sleeve 12 which would be held by a user. Removal of the protective needle shield 5 may be facilitated by a cap arranged on the proximal end P in the initial state, the cap engaged with the protective needle shield 5 (cap is not illustrated).

Figures 2A, 2B:
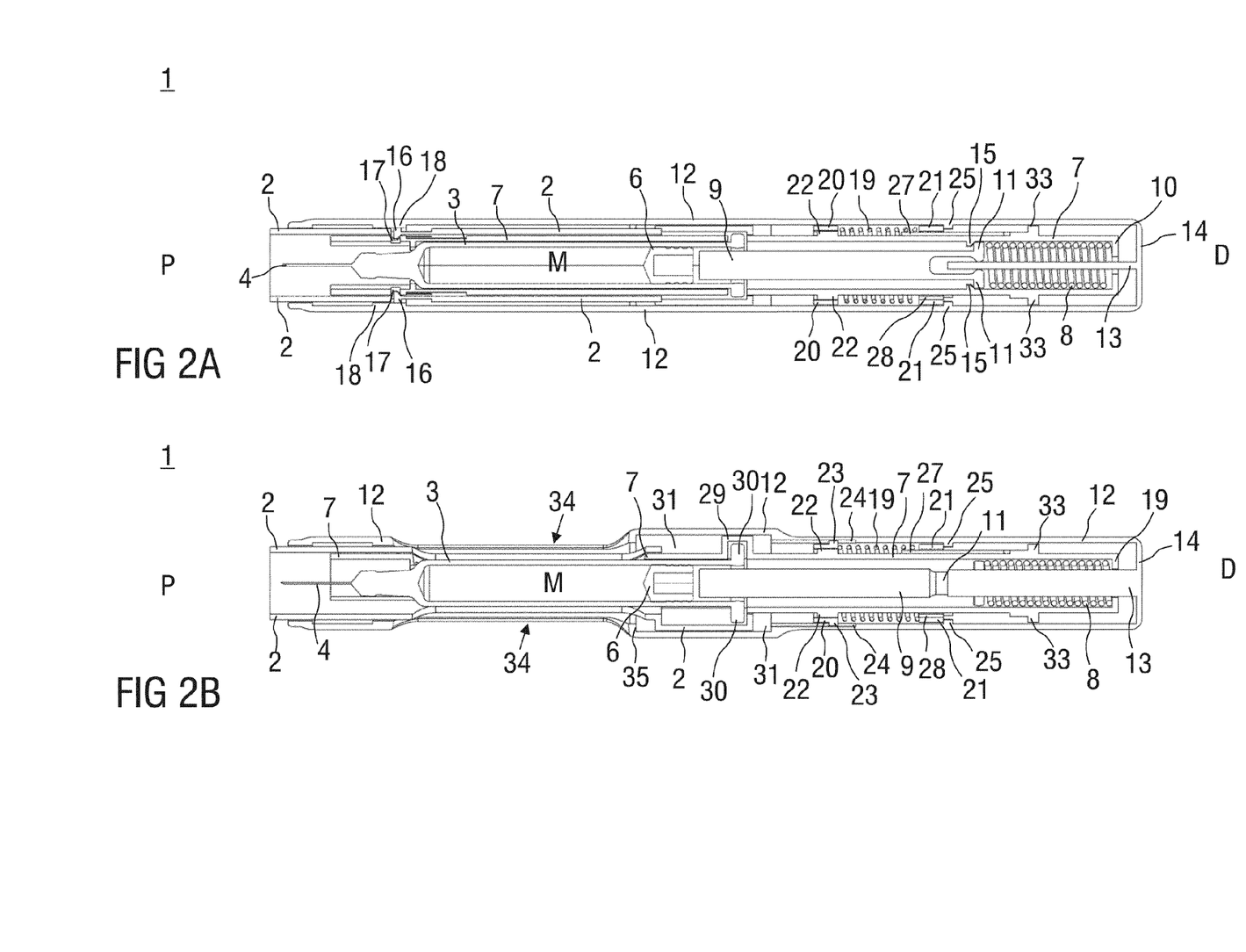
FIG. 2 is the auto-injector with a protective needle shield removed and pushed against an injection site.

In order to trigger an injection, the user, i.e. the patient or a caregiver places the proximal end P of the auto-injector 1 on the injection site, e.g. the patient's skin and pushes the trigger sleeve 12 against the injection site (see FIG. 2). The chassis 2, together with all internal parts, translates in distal direction D into the trigger sleeve 12. The user would visualise this translation of the chassis 2 as depression of a skin-contact shroud. The control spring 19 opposes this motion but is specified such that its spring rate and preload are low enough for this to feel natural. This translation is completely reversible, i.e. the user can place the auto-injector on the injection site, depress the chassis 2 (skin-contact-shroud) and remove the auto-injector 1 from the injection site without activating it, thereby allowing the chassis 2 and the trigger sleeve 12 to return to their initial position under load of the control spring 19.

The auto-injector 1 may optionally have a two-stage firing mechanism. In this case, further translation from the position in FIG. 2 would be opposed by a detent mechanism (not illustrated).

Figure 3A:
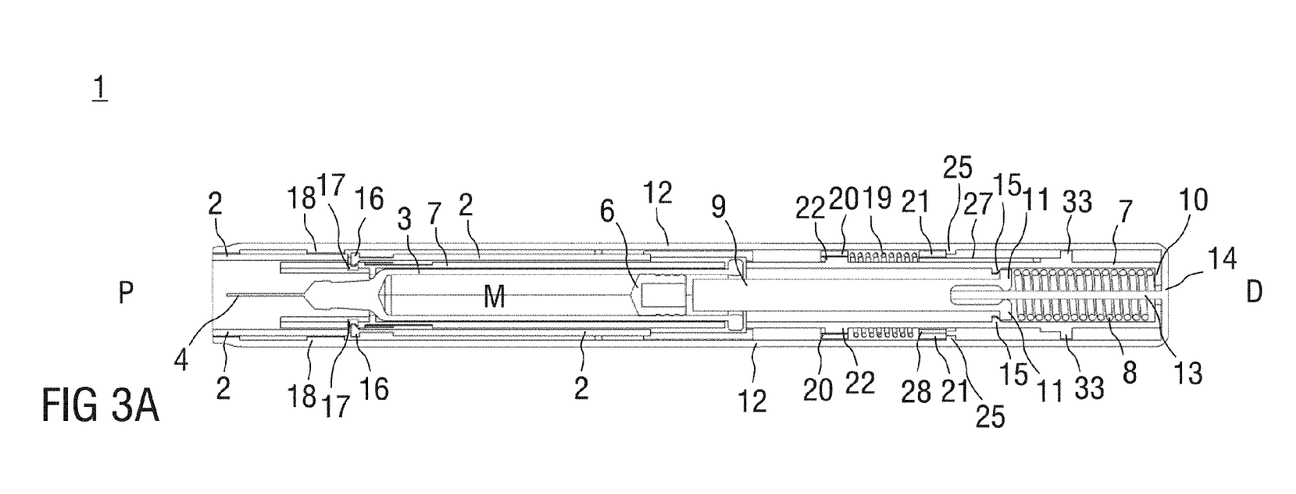
FIG. 3 is the auto-injector with a trigger sleeve button fully depressed.
Figure 3B:
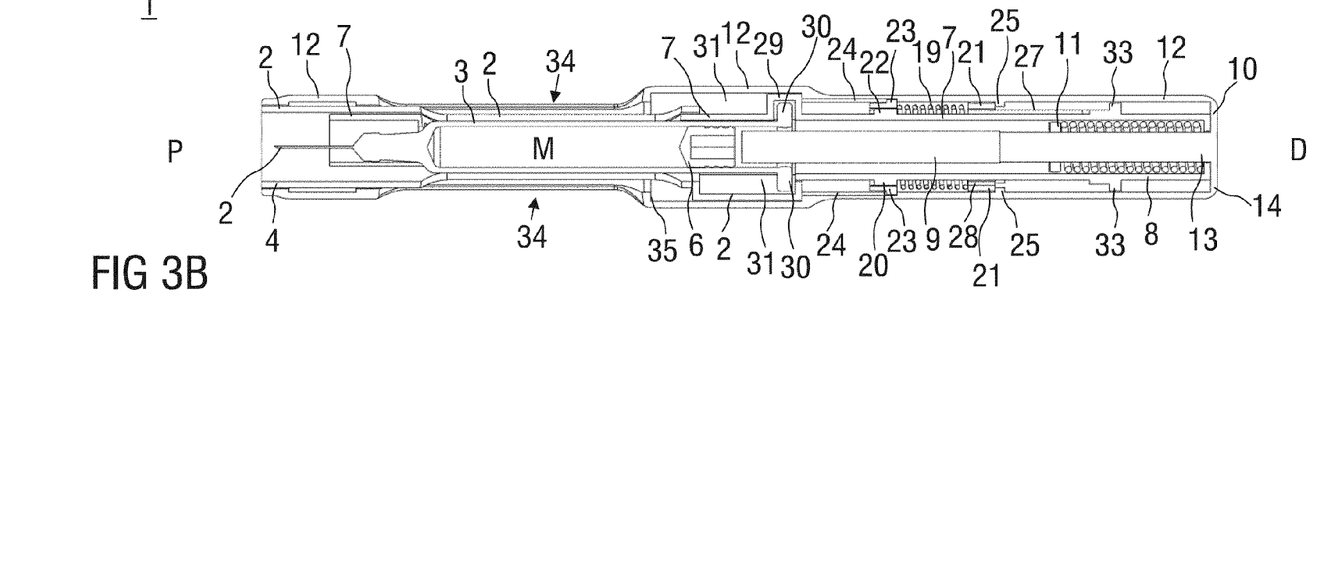

When ready to do so, the user continues to push the proximal end P of the auto-injector against the injection site while holding the trigger sleeve 12. The chassis 2, together with all the internal parts locked to it moves relative to the trigger sleeve 12 in distal direction D until the carrier end face 10 comes into contact with a trigger end face 14 at the distal end D of the auto-injector 1 (see FIG. 3).

Figure 4A:
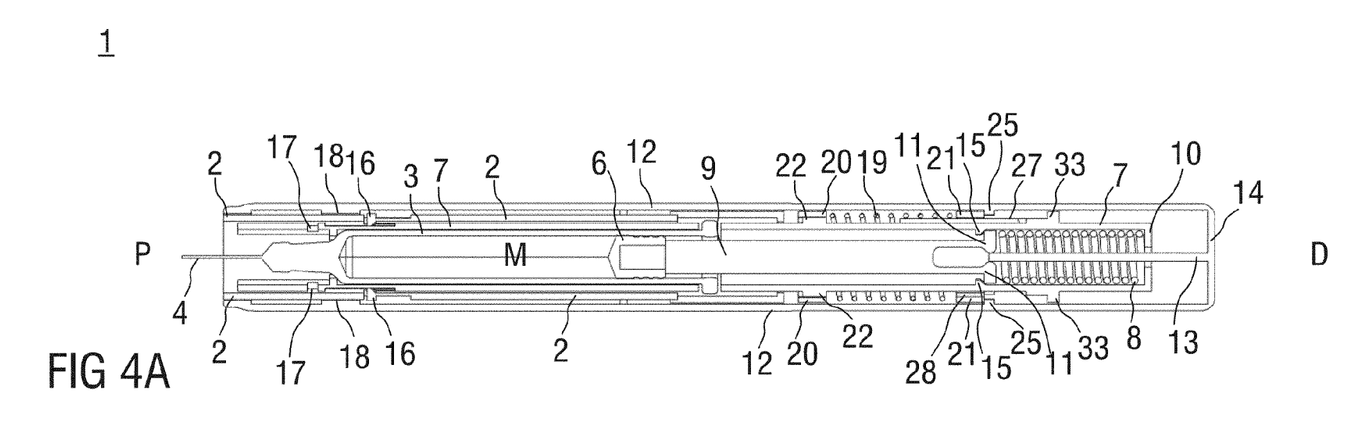
FIG. 4 is the auto-injector with an injection needle inserted into the injection site.
Figure 4B:
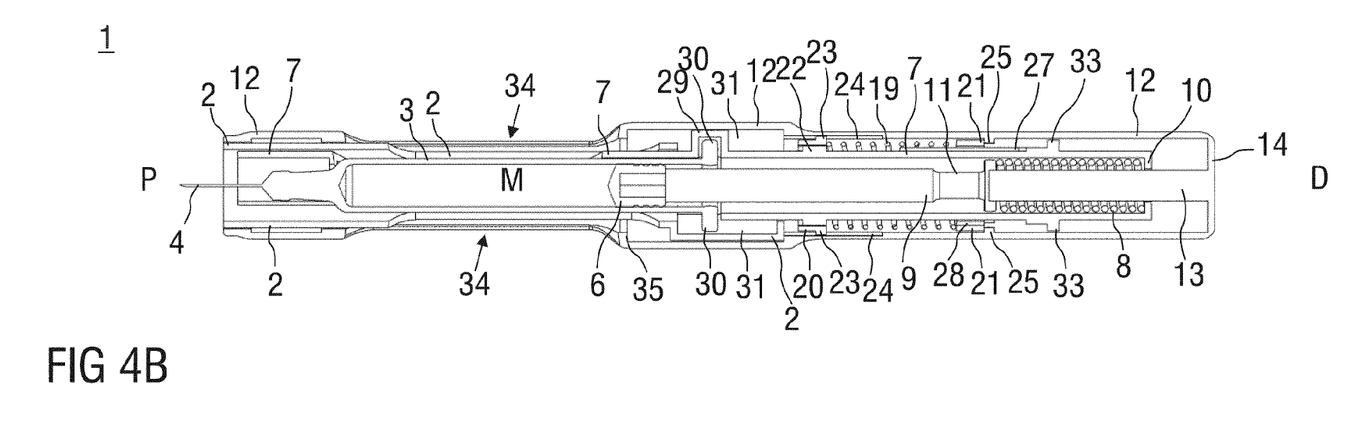

Just before this position is reached, the second boss 18 locking the carrier 7 to the chassis 2 has moved to a position where the second resilient clip 16 is allowed to flex outwards due to its ramped engagement with the carrier 7, which is biased in proximal direction P by the control spring 19 pushing against the proximal collar 20. The lock between the chassis 2 and the carrier 7 is thus released. The control spring 19 then forces the carrier 7 to move in proximal direction P along with the syringe 3 and the needle 4 thus inserting the needle 4 into the injection site (see FIG. 4).

Figure 5A:
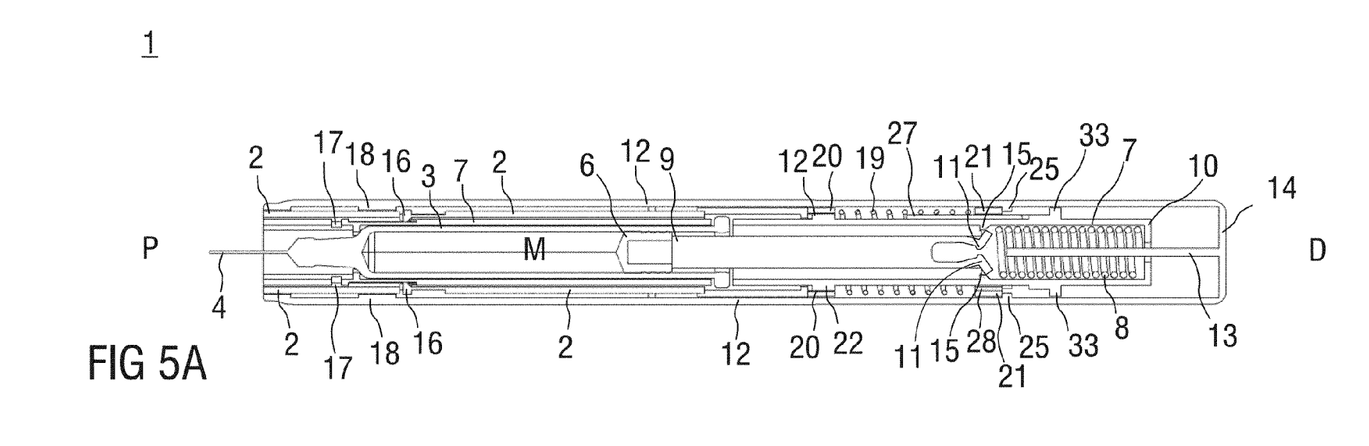
FIG. 5 is the auto-injector with a drive spring released for injection.
Figure 5B:
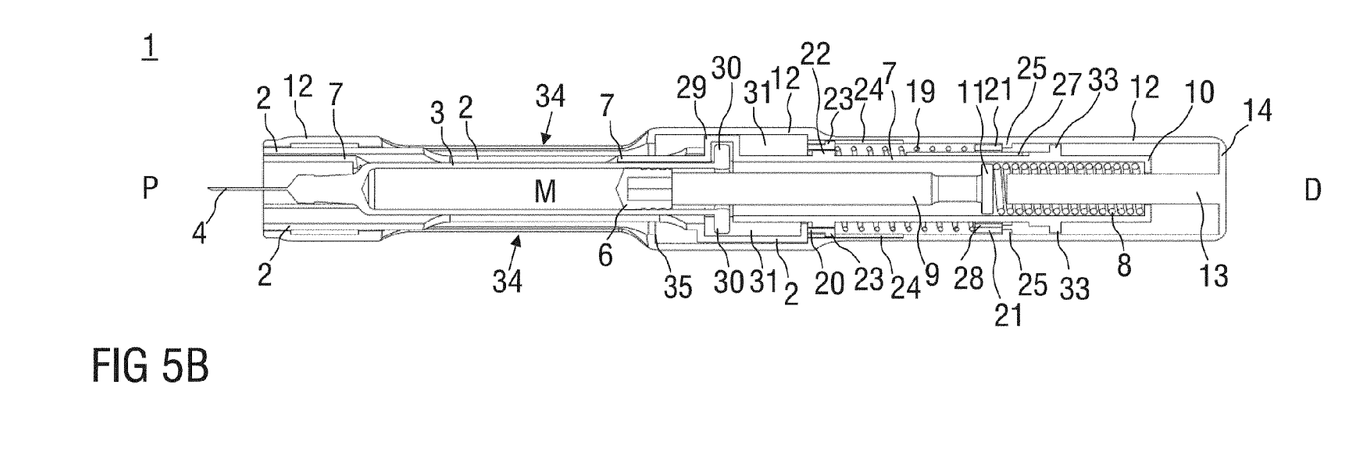

FIG. 5 shows the carrier 7, the syringe 3 and the needle 4 fully advanced into a maximum proximal position defining an injection depth. This maximum proximal position is limited by contact of the retainer pocket 29 with the chassis 2 (see FIG. 5a). Just before the maximum proximal position is reached, the carrier 7, syringe 3, needle 4, drive spring 8 and plunger 9 have translated relative to the trigger sleeve 12 so far that the first bosses 13 do no longer support the first resilient clips 15 thus allowing the thrust collar 11 to flex the first resilient clips 15 out due to their ramped engagement under load of the drive spring 8 thus releasing the plunger 9. The plunger 9 starts translating in proximal direction P under load of the drive spring 8. The drive spring 8 expands, the plunger 9 contacts the stopper 6 and the medicament M is expelled through the needle 4.

Figure 6A:
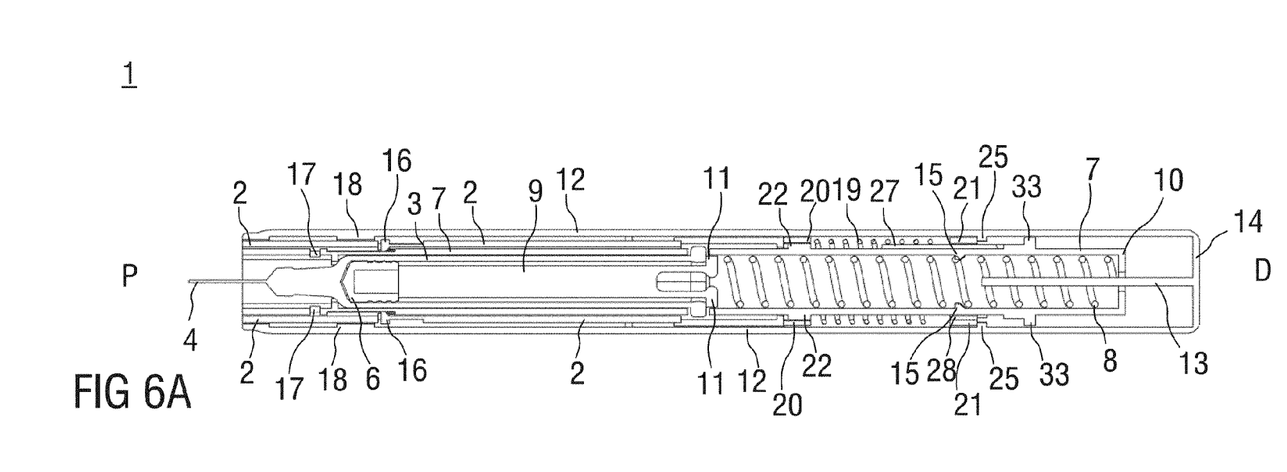
FIG. 6 is the auto-injector with the syringe emptied.
Figure 6B:
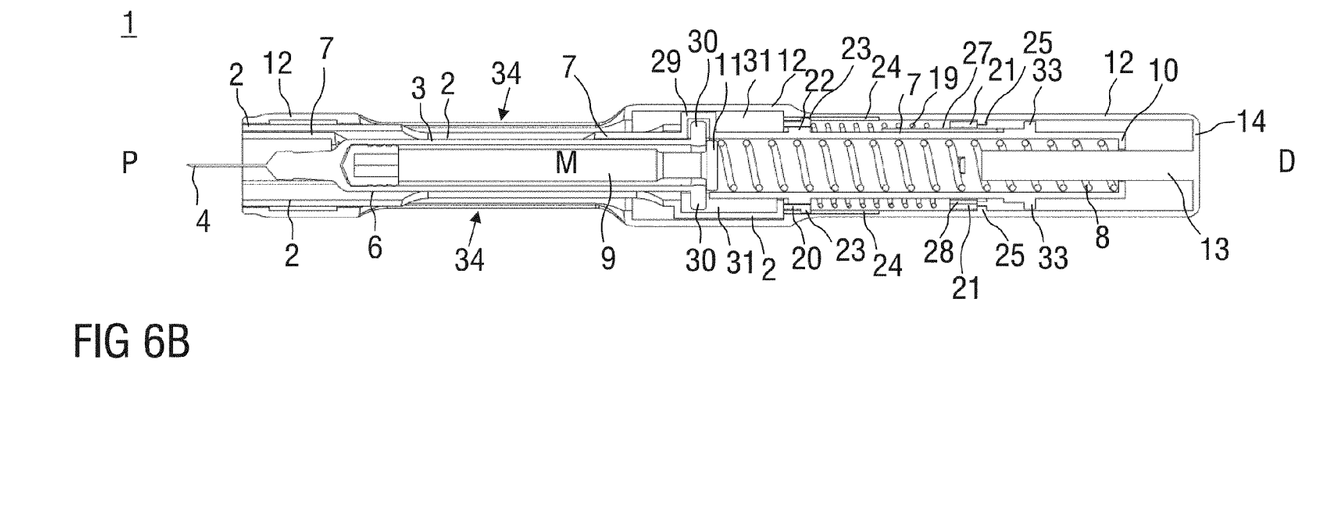

This motion of the stopper 6 continues until the stopper 6 bottoms out in the syringe 3, thereby fully emptying the syringe 3. The user would be asked to keep pressure on the injection site for a short period of time, e.g. ten seconds to ensure this is achieved (see FIG. 6).

As the user withdraws the auto-injector 1 from the injection site, the chassis 2 together with all internal components extend out of the trigger sleeve 12 in proximal direction D by the control spring 19 acting between rib 21 on the trigger sleeve 12 and the proximal collar 20 locked to the carrier 7. The second resilient clip 16 returns to its original radial position to allow the second boss 18 to pass back over it when trigger sleeve 12 moves in the distal direction D on removal from the injection site. The needle 4 is not yet withdrawn from the injection site during this motion since this would make the auto-injector 1 sensitive to the motion of the trigger sleeve 12 relative to the injection site during delivery of the medicament M.

Figure 7A:
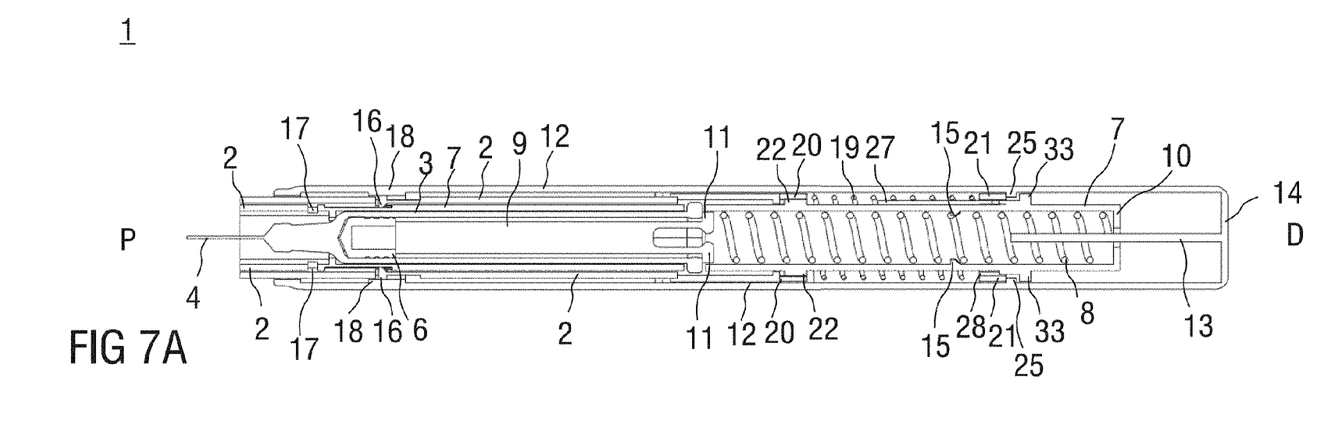
FIG. 7 is the auto-injector removed from the injection site after the end of injection.

As the chassis 2 extends to the initial pre-injection position as in FIG. 1, the third boss 24 on the trigger sleeve 12 locking the proximal collar 20 to the carrier 7 moves out of the way in distal direction D thus allowing the pin 22 to disengage from the first recess 23 due to their ramped engagement under load of the control spring 19 (see FIG. 7). The proximal collar 20 is thus released from the carrier 7. The load on the proximal end of the control spring 19 is now applied to the chassis 2.

As the chassis 2 continues to move in proximal direction P it reaches its initial pre-injection position, however the stop is no longer active as the fourth boss 27 on the carrier 7 has moved out of the way during needle insertion. Instead, the third resilient clip 25 is flexed inwards into a second recess 28 in the carrier 7 due to its ramped engagement with the first shoulder 26. On continued translation of the chassis 2 in proximal direction P with respect to the trigger sleeve 12 the third resilient clip 25 flexes outwards again behind the first shoulder 26. The chassis 2 continues to extend out of the proximal end of the trigger sleeve 12.

Figure 8A:
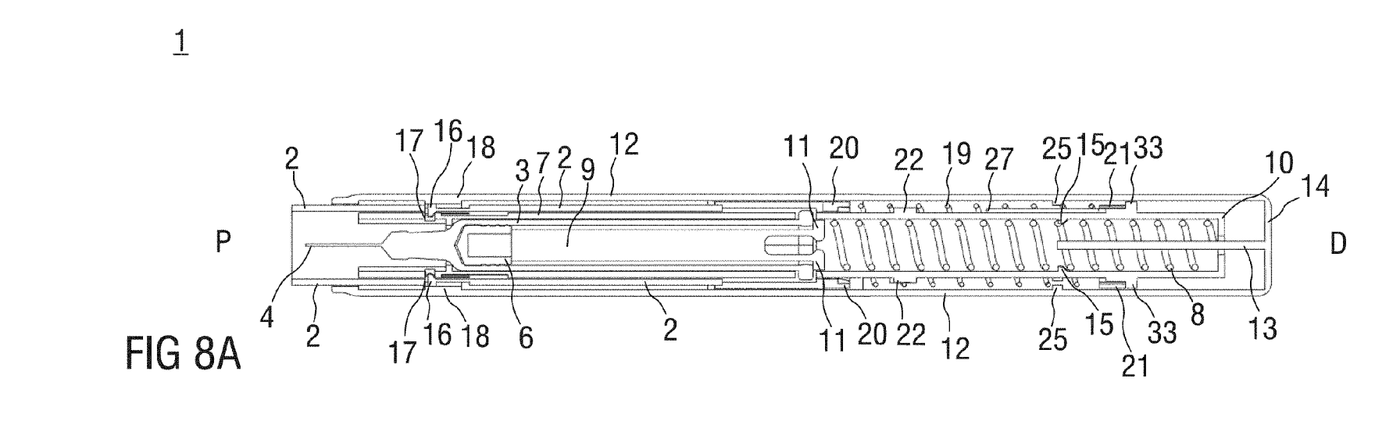
FIG. 8 is the auto-injector with a chassis advanced for covering the needle.
Figure 8B:
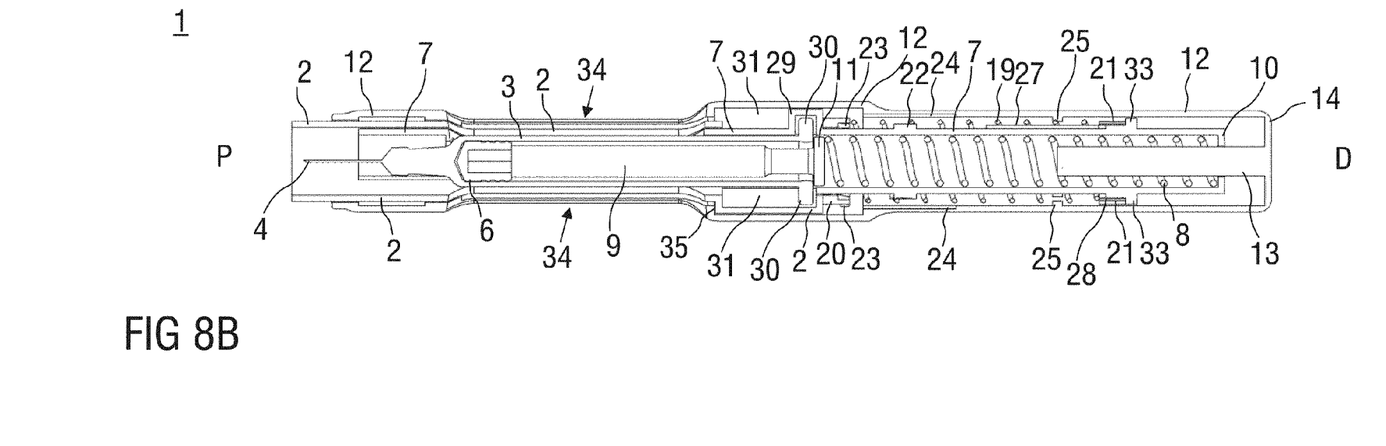
Figure 9:
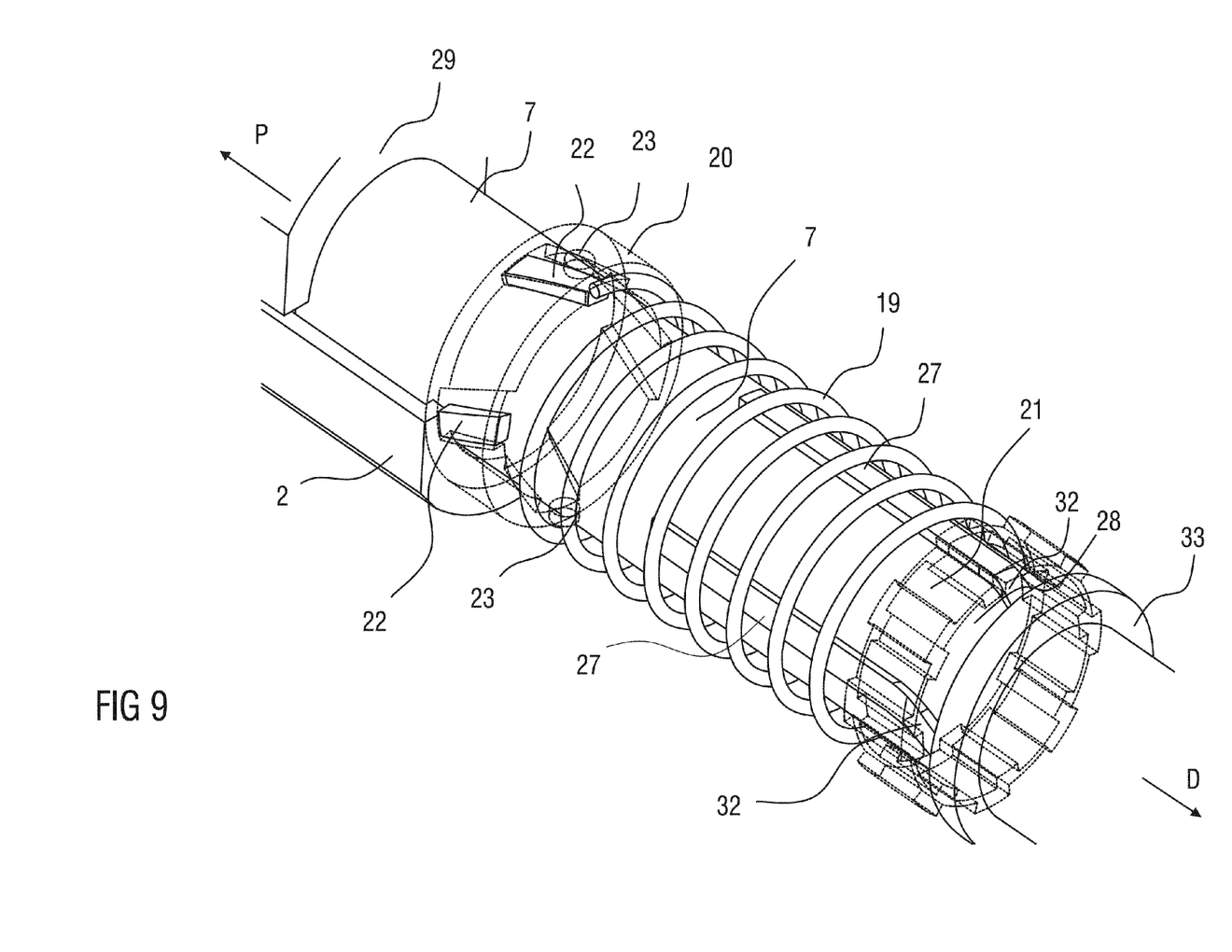
FIGS. 9 and 10 are perspective views showing a control spring arranged around a carrier.
Figure 10:
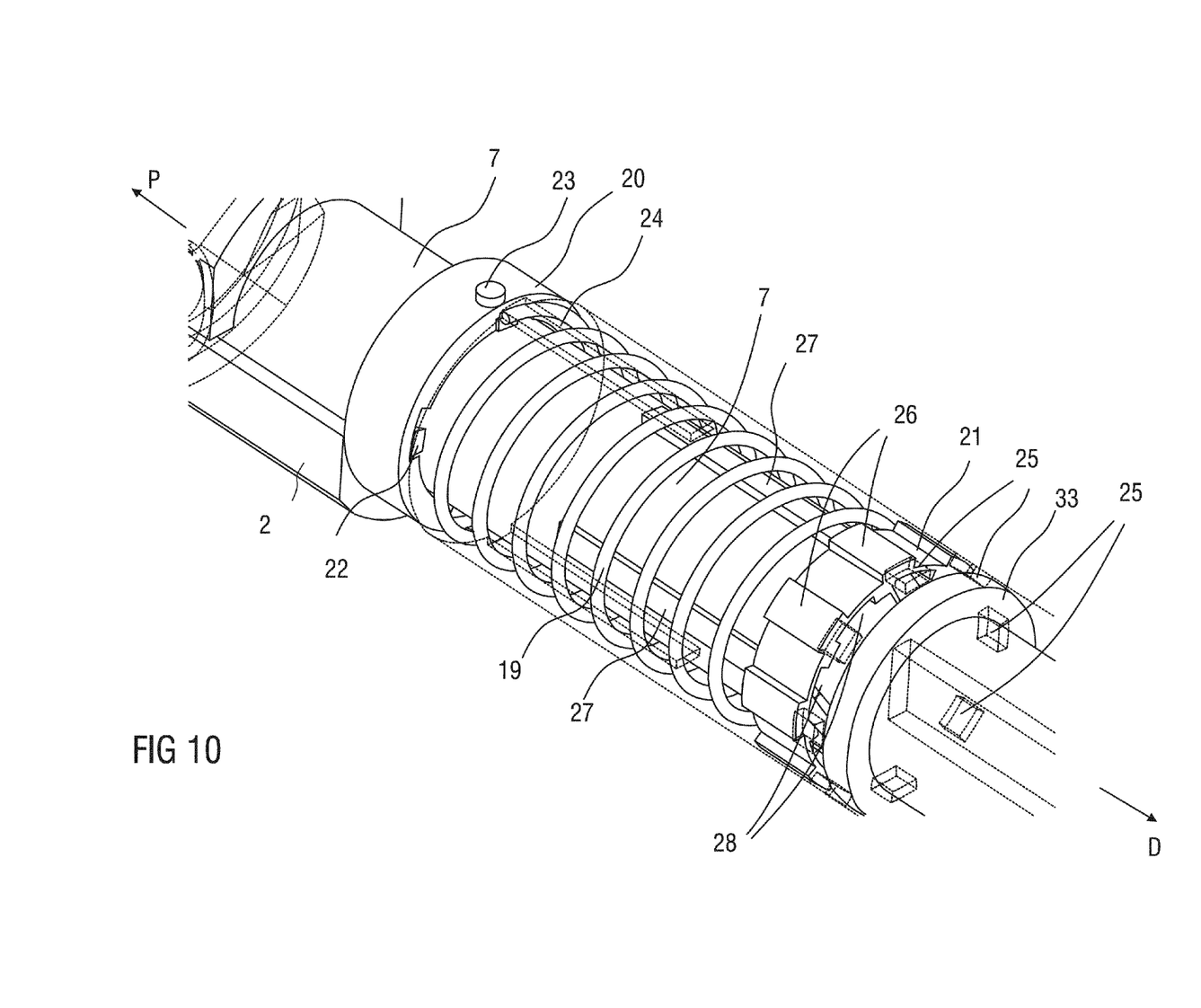

As the chassis 2 protrudes beyond its initial pre-injection position it can no longer restrict further translation of the carrier 7 and the needle 4 in proximal direction P. Instead, further substantial translation of the carrier subassembly is restricted by the distal end of the control spring 19 coming into contact with a flange 32 on the carrier 7. The distal end of the control spring 19 would then apply a load to both the trigger sleeve 12 and the carrier 7. This holds the carrier 7 and syringe 3 in the position as in FIG. 8 within the auto-injector 1. In the illustrated embodiment, there is no additional lock to prevent the carrier 7 re-emerging under inertial loading. It would be possible to introduce a lock with a snap feature between the trigger sleeve 12, the chassis 2 and the carrier 7 to ensure the syringe 3 is held back within the auto-injector 1.

If the user were to remove the auto-injector 1 from the injection site prior to full syringe emptying, the described motion of the chassis 2 would still be achieved. However, in that case the syringe 3 would be fully emptied after removal from the injection site.

Acting between the carrier 7/trigger sleeve 12 and the chassis 2, the control spring 19 continues to force the chassis 2 out of the proximal end P of the auto-injector 1. The auto-injector 1 is now longer than in the initial state.

A viewing window may be arranged in the shape of apertures in the trigger sleeve 12, in the chassis 2 and in the carrier 7 for inspecting the syringe contents.

The invention claimed is:

1. Auto-injector for administering a dose of a liquid medicament (M), comprising:
   a tubular chassis arranged to contain a syringe with a hollow needle and a stopper for sealing the syringe and displacing the medicament (M), the chassis having a distal end (D) and a proximal end (P) with an orifice intended to be applied against an injection site, wherein the syringe is slidably arranged with respect to the chassis,
   a drive spring capable of operating the syringe to supply the dose of medicament (M),
   a control spring capable of
   pushing the needle from a covered position inside the chassis into an advanced position through the orifice and past the proximal end (P) for needle insertion, and
   advancing the chassis over the needle after at least partially delivering the medicament (M),
   an activating sleeve arranged to lock the drive spring and the control spring in a pressurized state prior to manual operation and capable of, upon manual operation, releasing the control spring and/or the drive spring for injection, wherein a carrier subassembly, comprising a tubular carrier is slidably arranged in the chassis, the carrier containing the syringe, the drive spring and a plunger for forwarding load of the drive spring to the stopper, wherein the syringe is locked for joint axial translation with the carrier, wherein the control spring is connectable to the carrier by a first interlock collar for needle insertion, wherein the activating sleeve comprises a second interlock collar arranged for releasing the drive spring when the carrier has at least almost reached an injection depth and wherein the first interlock collar is arranged for decoupling the control spring from the carrier and coupling it to the chassis for advancing it over the needle into a needle safe position.

2. Auto-injector according to claim 1, wherein the activating sleeve comprises a wrap-over trigger sleeve arranged over the distal end (D) of the auto-injector, the trigger sleeve extending at least almost over the whole length of the auto-injector, wherein the trigger sleeve is arranged to release the control spring upon translation in proximal direction (P) relative to the chassis.

3. Auto-injector according to claim 2, wherein a third interlock clip is arranged for coupling the chassis to the carrier for joint axial translation relative to the trigger sleeve, wherein the third interlock clip is arranged to decouple the chassis from the carrier upon translation of the trigger sleeve in proximal direction (P) thus releasing the control spring for needle insertion.

4. Auto-injector according to claim 3, wherein the third interlock clip comprises at least one second resilient clip on the chassis arranged to be engaged in a respective aperture in the carrier, wherein a respective second boss is arranged in the trigger sleeve for outwardly supporting the second resilient clip and preventing it from flexing outwards, wherein the second boss is arranged to be removed from behind the second resilient clip on translation of the chassis and the carrier subassembly in distal direction (D) relative to the trigger sleeve during manual operation into a position just before the carrier abuts against the trigger sleeve thereby allowing the second resilient clip to flex outwards due to ramped engagement with the carrier under load of the control spring thus releasing the carrier subassembly from the chassis.

5. Auto-injector according to claim 3, wherein a detent mechanism is provided for opposing translation of the chassis in distal direction at a point before the release of the third interlock clip.

6. Auto-injector according to claim 2, wherein the control spring is arranged around the carrier, wherein the first interlock collar comprises a proximal collar arranged around the carrier proximally from the control spring, wherein the control spring acts between the trigger sleeve and the proximal collar, wherein the proximal collar exhibits at least one pin engageable in a respective first recess in the carrier for coupling the proximal collar to the carrier, wherein the trigger sleeve exhibits a third boss for outwardly supporting the proximal collar so as to prevent decoupling of the pin from the first recess, wherein the carrier is arranged to extend out of the proximal end of the trigger sleeve under load of the control spring when the auto-injector is being removed from the injection site thereby removing the third boss from behind the proximal collar thus causing the pin to decouple from the first recess due to ramped engagement and to be coupled to the chassis for advancing it over the needle.

7. Auto-injector according to claim 6, wherein a fourth interlock clip is arranged for restricting extension of the chassis from the proximal end of the trigger sleeve to an initial pre-injection position, wherein the fourth interlock clip is arranged to disengage upon translation of the carrier subassembly during needle insertion.

8. Auto-injector according to claim 7, wherein the fourth interlock clip comprises at least one third resilient clip on the chassis arranged to abut against a shoulder in the trigger sleeve in proximal direction (P), wherein a fourth boss is arranged on the carrier for inwardly supporting the third resilient clip and preventing it from flexing inwards, wherein the fourth boss is arranged to be removed from behind the third resilient clip on translation of the carrier subassembly in proximal direction (P) relative to the chassis during needle insertion thereby allowing the third resilient clip to flex inwards due to ramped engagement with the fourth boss under load of the control spring thus allowing the chassis to travel beyond the initial pre-injection position into a needle safe position.

9. Auto-injector according to claim 1, wherein the second interlock collar comprises a thrust collar distally arranged on the plunger, the thrust collar having a wider diameter than the plunger, wherein the drive spring acts between the thrust collar and the carrier, wherein at least one first resilient clip is arranged in the carrier, the first resilient clip proximally engageable behind the thrust collar for preventing translation of the plunger, wherein a first boss in the trigger sleeve is arranged for outwardly supporting the first resilient clip and preventing it from flexing outwards, wherein the first boss is arranged to be removed from behind the first resilient clip on translation of the carrier subassembly at least almost into a maximum proximal position during needle insertion, thereby allowing the first resilient clip to be flexed outwards by the thrust collar due to ramped engagement under load of the drive spring thus releasing the plunger for injection.

10. Auto-injector according to claim 1, wherein a flange is arranged on the carrier for abutting against the distal end of the control spring so as to prevent the carrier subassembly from advancing substantially beyond its maximum proximal position when the chassis has been advanced over the needle.

11. Auto-injector according to claim 1, wherein a snap feature is provided between the chassis and the carrier for locking them together when the chassis is in the needle safe position.

12. Auto-injector according to claim 1, wherein the injection depth is defined by the carrier contacting the chassis.

13. Method for operating an auto-injector, the auto-injector comprising a tubular chassis and a carrier subassembly comprising a tubular carrier slidably arranged in the chassis, the carrier containing a syringe, a drive spring and a plunger for forwarding load of the drive spring to a stopper of the syringe, wherein the syringe is locked for joint axial translation with the carrier, wherein a control spring is arranged around the carrier inside a wrap-over trigger sleeve arranged over the distal end (D) of the auto-injector and extending at least almost over the whole length of the auto-injector, wherein a first interlock collar is arranged to connect a proximal end of the control spring to the carrier or to the chassis depending on a relative axial position of the carrier and the trigger sleeve, wherein a distal end of the control spring is connected to the trigger sleeve, wherein a second interlock collar is arranged to prevent or allow release of the drive spring depending on a relative axial position of the trigger sleeve and the carrier, the method comprising the steps of:

coupling the control spring to the carrier by the first interlock collar and preventing release of the drive spring by the second interlock collar in an initial state, translating the trigger sleeve in proximal direction (P) relative to the chassis against the force of the control spring when the proximal end (P) of the auto-injector is being pushed against an injection site, advancing the carrier subassembly for insertion of a hollow injection needle on the syringe into an injection site upon full translation of the trigger sleeve, releasing the drive spring by the second interlock collar when the needle at least almost reaches an injection depth during needle insertion, thereby allowing the drive spring to advance the plunger and the stopper for at least partially delivering the medicament (M), translating the trigger sleeve in distal direction (D) under load of the control spring relative to the carrier subassembly on removal of the auto-injector from the injection site, thereby connecting the control spring to the chassis by the first interlock collar, advancing the chassis in proximal direction (P) relative to the carrier subassembly into a needle safe position under load of the control spring.

14. Method according to claim 5, wherein a third interlock clip is arranged for coupling the chassis to the carrier for joint axial translation relative to the trigger sleeve depending on a relative axial position of the trigger sleeve and the chassis, wherein the third interlock clip is released thereby decoupling the chassis from the carrier upon translation of the trigger sleeve in proximal direction (P) thus releasing the control spring for needle insertion.

15. Method according to claim 5, wherein fourth interlock clip is arranged for restricting extension of the chassis from the proximal end of the trigger sleeve to an initial pre-injection position depending on a relative axial position of the carrier and the chassis, wherein the fourth interlock clip is disengaged upon translation of the carrier subassembly during needle insertion.

* * * * *